United States Patent [19]
Björnberg et al.

[11] Patent Number: 4,892,535
[45] Date of Patent: Jan. 9, 1990

[54] ABSORBENT PAD AND METHOD AND APPARATUS FOR MAKING THE SAME

[75] Inventors: Sten Björnberg, Spånga; Ove Ahlstrand, ålvsjö, both of Sweden

[73] Assignee: Landstingens Inköpscentral, Lic, Ekonomisk Förening, Solna, Sweden

[21] Appl. No.: 82,725

[22] Filed: Aug. 7, 1987

[51] Int. Cl.⁴ ............................................. A61F 13/16
[52] U.S. Cl. .................... 604/380; 604/366; 604/370
[58] Field of Search ............... 604/358, 380, 366, 379, 604/369, 370, 365, 368, 374; 206/204

[56] References Cited

U.S. PATENT DOCUMENTS

| | | | |
|---|---|---|---|
| Re. 30,972 | 6/1982 | Kyle et al. | 428/219 |
| D. 247,368 | 2/1978 | Whitehead | D24/51 |
| 2,627,858 | 2/1953 | Miller | 604/365 |
| 2,952,260 | 9/1960 | Burgeni | 604/374 |
| 2,978,006 | 4/1961 | Clemens | 156/210 |
| 3,060,936 | 10/1962 | Burgeni | 604/365 |
| 3,221,738 | 12/1965 | Ekberg et al. | 604/366 |
| 3,315,676 | 4/1967 | Cooper | 604/366 |
| 3,670,345 | 6/1972 | Doll et al. | 5/484 |
| 3,729,005 | 4/1973 | Lee et al. | 604/366 |
| 3,881,487 | 5/1975 | Schrading | 604/365 |
| 3,881,490 | 5/1975 | Whitehead et al. | 604/366 |
| 4,033,709 | 7/1977 | Kroyer | 425/224 |
| 4,059,114 | 11/1977 | Richards | 604/359 |
| 4,079,739 | 3/1978 | Whitehead | 604/365 |
| 4,211,227 | 7/1980 | Anderson et al. | 428/198 |
| 4,275,811 | 6/1981 | Miller | 206/204 |
| 4,321,997 | 3/1982 | Miller | 206/204 |
| 4,327,732 | 5/1982 | Thinnes | 604/370 |
| 4,331,501 | 5/1982 | Teed | 156/383 |
| 4,338,366 | 7/1982 | Evans et al. | 428/76 |
| 4,360,021 | 11/1982 | Stima | 428/68 |
| 4,381,783 | 5/1983 | Elias | 604/368 |
| 4,382,507 | 5/1983 | Miller | 206/204 |
| 4,392,862 | 7/1983 | Marsan et al. | 604/366 |
| 4,560,372 | 12/1985 | Pieniak | 604/369 |
| 4,650,481 | 3/1987 | O'Connor et al. | 604/366 |

FOREIGN PATENT DOCUMENTS

| | | |
|---|---|---|
| 0030342 | 6/1981 | European Pat. Off. . |
| 433562 | 6/1984 | Sweden . |
| 2100130 | 12/1982 | United Kingdom ............... 604/358 |

*Primary Examiner*—James C. Yeung
*Attorney, Agent, or Firm*—Young & Thompson

[57] ABSTRACT

An absorbent pad such as an incontinence pad comprises a liquid-impervious back sheet with spaced islands of absorbent material thereon. A liquid-pervious cover sheet has pockets formed therein, in which the islands of absorbent material are disposed. The cover sheet is secured, either adhesively or by heat sealing, directly to the impervious sheet along lines that separate the islands of absorbent material and the pockets that contain them. The pad is formed by applying a strip of cover sheet material to a rotating multi-perforate drum and forming the pockets in the cover sheet material either mechanically, or by drawing hot air inwardly through the holes in the drum in the case of a heat-deformable material such as polypropylene fibers. The drum then rotates past a pocket-filling station, where absorbent material such as cellulose fluff is drawn into the pockets by vacuum applied internally of the drum. The cover sheet is then applied to the composite of cover sheet and absorbent material, and is firmly bonded to lines of cover sheet material that are free from absorbent material between the pockets, overlying the bridges that separate the holes through the drum. The composite is then removed from the drum and cut to size.

5 Claims, 3 Drawing Sheets

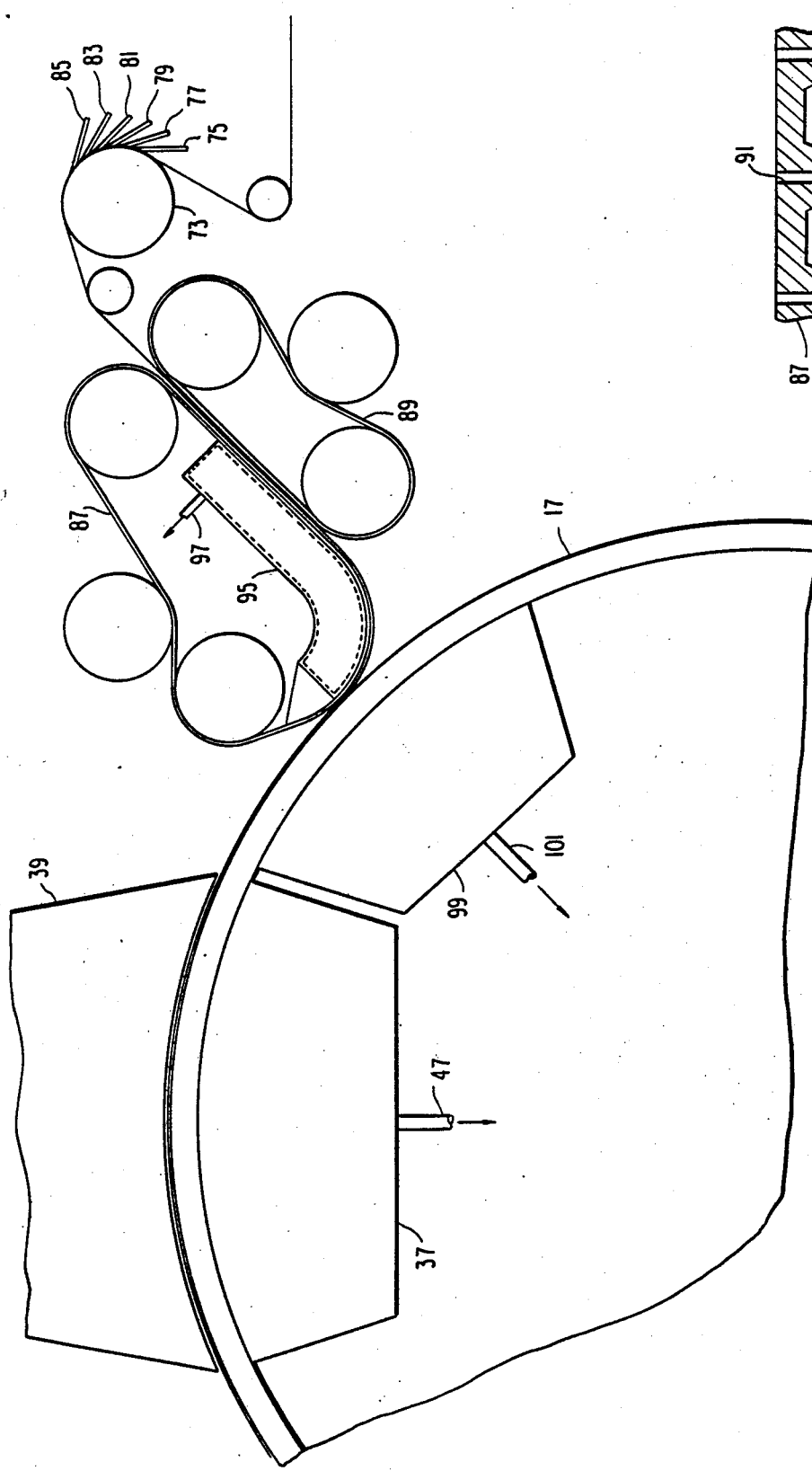
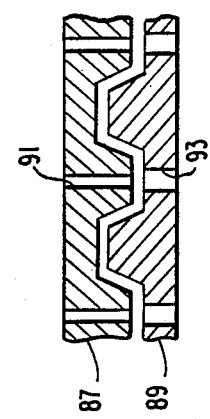
FIG. 7
FIG. 6

ABSORBENT PAD AND METHOD AND APPARATUS FOR MAKING THE SAME

FIELD OF THE INVENTION

The present invention relates to absorbent pads and methods and apparatus for making the same, more particularly absorbent pads of the type used as incontinence pads to be positioned under persons needing the same.

BACKGROUND OF THE INVENTION

It is known to make absorbent pads with flow-spreading depressions or projections. Sanitary napkins, baby diapers and the like have been made with cellulose fluff or crepe wadding material between a cover sheet and a plastic back sheet, and with the absorbent medium embossed with depressions extending parallel to the longitudinal axis of the pad, transverse thereto, or in various patterns such diamond, herringbone, sinusoidal, etc. Examples of methods and apparatus for making such products are shown in U.S. Pat. Nos. 2,627,858, 2,978,006, 3,221,738, 3,315,676, 3,670,345, 3,729,005, 4,033,709, 4,275,811, 4,382,507 and 4,392,862.

These patents teach the embossing of a continuous mat of absorbent material by depressing a portion of the mat under an embossing roller having the required pattern to create the channels of the intended configuration. This not only created flow channels, but also helped to integrate the mat and prevent balling of the cellulose into one end of the bag created by the cover and back sheets. A method and machine for creating such embossed channels is shown in U.S. Pat. No. 4,331,501.

Various patterns and designs of the flow channels themselves are shown in U.S. Pat. Nos. 3,881,490, 4,059,114, 4,079,739, 4,211,227 4,381,783, and Des. 247,368.

It is also known to moisten the cellulose under the embossing roller so as to increase the density of the cellulose and improve the wicking or flow spreading characteristics of the channels. This is disclosed in U.S. Pat. Nos. 2,952,260 and 3,060,936.

It is further known to apply these principles to hospital bed pads, rather than to diapers, as shown by U.S. Pat. Nos. 4,327,732 and Re. 30,972.

In all of these products, the absorbent mat was continuous prior to embossing and so was continuous after embossing, that is, the mat was not separated into separate islands but extended continuously between the cover and back sheets and across the channel regions.

A variation on the constructions discussed above involved the application of lines of glue or other adhesive to the plastic backing sheet to hold the absorbent mat in place. Usually such lines were parallel to the longitudinal extent of the pad, but a diamond pattern is shown in U.S. Pat. No. 3,881,487. In this patent, the channels are filled with adhesive and thus the flow of liquid through the channels is impeded.

It is further known, as in U.S. Pat. No. 4,321,997, to provide diamond-shaped islands of absorbency isolated by a lattice-like network of plastic net which fills the channels between the islands and so does not provide flow-enhancing grooves.

Islands of absorbent material are also shown in U.S. Pat. No. 4,338,377, held between two sheets of web material.

U.S. Pat. No. 4,560,372 discloses a pad wherein a lattice-like network of absorbent fibers and superabsorbent material is expanded to form areas of absorbency in the channels with the islands between such areas being void.

Finally, U.S. Pat. No. 4,360,021 discloses an embossed plastic sheet which provides tiny depressions having small quantities of superabsorbent material in the depressions. A cover of non-woven material is disposed over the depressions and the liquid is discharged directly onto the cover and into the depressions. As one depression is filled and the liquid absorbed by the filling material, excess liquid spills over into the next adjacent depression, and continues until the liquid is fully absorbed in the nearest depressions. Such a structure has no channels for flow of the liquid.

OBJECTS OF THE INVENTION

It is accordingly an object of the present invention to provide an absorbent pad, for example of the incontinence pad type, having improved characteristics of liquid flow and absorption.

Another object of the present invention is the provision of such a pad, whose construction reduces the chance of liquid leakage or spillage.

Still another object of the present invention is the provision of such a pad, which will be easy and inexpensive to manufacture and rugged and durable in use.

A further object of the present invention is the provision of a method for making such pads.

Finally, it is an object of the present invention to provide apparatus for making such pads.

SUMMARY OF THE INVENTION

An absorbent pad according to this invention comprises a liquid-impervious back sheet having a plurality of bodies of absorbent material on one side thereof, held in place by a liquid-pervious cover sheet. The bodies are separated by channels along which the cover sheet is directly secured to the back sheet, these channels being substantially free from absorbent material. The cover sheet between the channels is of three-dimensional form, having a plurality of spaced pockets therein, in each of which one of the bodies of absorbent material is disposed.

The channels between the pockets of absorbent material provide liquid passageways which are unobstructed when a person is sitting or lying on the pad. The absorbent material in the pockets is easily accessible to the liquid flowing in the channels, through the cover sheet that forms the side walls of those channels. As the pockets directly under the body of the person becomes saturated with liquid flowing from the body, the excess liquid flows through the channels to the next available absorbent pocket.

To make such a pad, there is provided a method and apparatus according to which a supply of liquid- and gas-pervious cover sheet of indeterminate length is fed to the periphery of a multi-perforate drum whose holes match the size of the pockets to be formed. Pockets are formed in the cover sheet material, these pockets being disposed one in each hole in the drum. If the cover sheet is thermo-formable, as in the case of a thermoplastic resin, the pockets can be formed by drawing a vacuum on the radially inner side of the drum while supplying heated air from the radially outer side thereof, so that the heated air passes through the thermo-formable porous material and softens the same, the resistance to this passage exerting sufficient force on the material to form the pockets. In the case of a non-thermo-formable material, the pockets can be formed by mechanical embossing, or by creasing the material both lengthwise and transversely so as to provide an excess of material in both directions, and then drawing this excess material down into pockets by suction.

As the drum turns, the pre-formed pockets will move into a pocket filling station in which absorbent material such as a fluff of bleached sulphate pulp is drawn into the pockets, again by vacuum from the inner side of the drum. As the vacuum draws the fluff into the pockets, the material of the pockets serves as a filter, letting the air pass through toward the source of vacuum but retaining the absorbent material in the pockets. The surfaces of the cover sheet that overlie the bridge between the holes through the drum, however, are not subject to vacuum and so do not tend to accumulate absorbent material thereon.

A liquid-impervious back sheet is then applied and is secured directly to those portions of the cover sheet that overlie the bridges between the holes through the drum. This can be done by applying glue between the back sheet and the bridge portions of the cover sheet, or by heat welding.

The final product is finally stripped from the drum and is cut to size.

BRIEF DESCRIPTION OF THE DRAWINGS

The above and other objects and features of the present invention will be better understood from a consideration of the following detailed description, taken in connection with the accompanying drawings, in which:

FIG. 6 is a fragmentary diagrammatic view of another embodiment of apparatus for practicing the method and producing the product of the present invention; and FIG. 7 is an enlarged fragment of the coacting belts of FIG. 6.

DETAILED DESCRIPTION OF THE INVENTION

Figure 1:
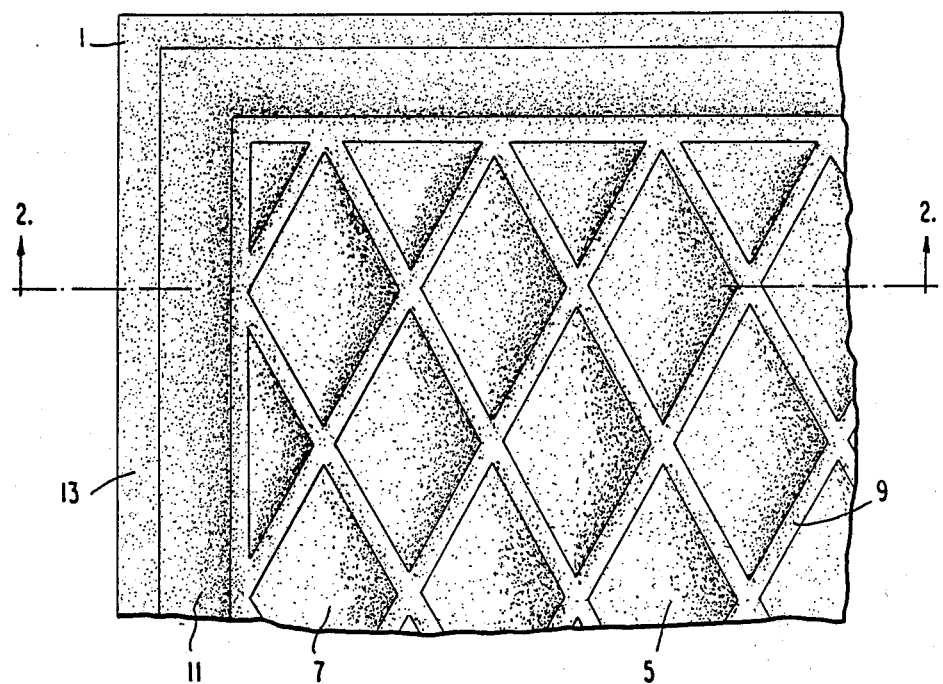
FIG. 1 is a top plan view of a fragment of an absorbent pad according to the present invention.
Figure 2:
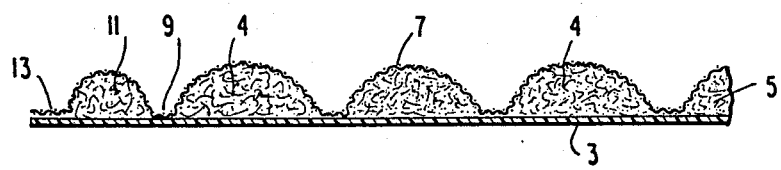
FIG. 2 is a cross sectional view thereof on the line 2—2 of FIG. 1.
Figure 3:
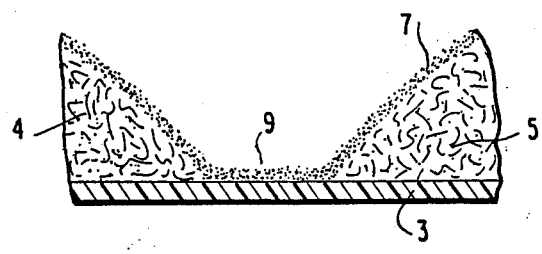
FIG. 3 is a view similar to FIG. 2 but showing a smaller portion thereof on a larger scale.

Referring now to the drawings in greater detail, and first to FIGS. 1–3 thereof, there is shown an absorbent pad 1 according to the present invention, in the form of an incontinence pad of the type used beneath the body of a human in need of the same. Pad 1 includes a liquid-impervious back sheet 3. The material of sheet 3 can be that which is conventionally used as the liquid-impervious back sheet for diapers and incontinence pads and the like, for example polyethylene film of a thickness of 0.010 mm to 0.050 mm, preferably 0.015 to 0.030 mm. A typical such material is DFDS 0601 of Neste AB of Sweden.

On top of sheet 3 are a plurality of spaced bodies 4 of absorbent material, preferably fibrous in nature. This absorbent material is quite conventional and has a high capacity to absorb liquid. A typical such absorbent is a fluff of bleached sulphate pulp made from softwood and having a fiber length of 0.1 mm to 10 mm, preferably 2–5 mm. Typical examples are "Billerud Fluff" from Stora of Sweden, and "Vigorfluff N" from Korsnas-Marma of Sweden. Such fluff typically has a bulk density of 18–31 $cm^3/g$ and can absorb up to ten times its weight in liquid. However, any other conventional absorbent could be used.

The bodies 4 are contained in pockets 5 formed in a continuous liquid-pervious cover sheet 7 that overlies the bodies 4 and is directly secured to back sheet 3 along channels 9 between bodies 4. The channels 9 thus define, in the illustrated embodiment, a diamond pattern. However, it will be obvious that squares, hexagons, triangles and other shapes could be defined by such channels. Although it is preferred that the channels define between them islands of absorbent material, that is, bodies 4 of absorbent material bounded on all sides by the channels, it is also within the purview of the invention that at least some of the bodies of absorbent material be more or less continuous. For example, it is within the invention to arrange at least some of the channels 9 in the form of an advertising symbol or logo.

When the bodies 4 are in the form of islands, it is preferred that they have a size from 10×10 mm up to 100×100 mm. A typical size for a diamond-shaped body as shown the drawings, is 62×28 mm. The bodies can also be elongated, having a length to width ratio from 1:1 up to 1:4 or even more.

The channels 9 can vary in width from 0.5 mm up to 10 mm, but are preferably 1–4 mm in width.

The pockets 5 can vary in depth from 1 mm to 20 mm or even more.

The cover sheet 7 can be woven or non-woven, preferably non-woven. A typical example of such non-woven material is extruded fibrous polypropylene, available among other places in the grade Holmestra from Holmen AB of Sweden. Such non-woven fabric is conventional in the art of disposable diapers and the like and has a weight of 10–35 $g/m^2$ or more.

However, the invention is not restricted to a non-woven cover sheet. Woven material is also within the contemplation of the invention. It follows from this that the invention is not restricted to disposable pads, but includes also reusable pads whose absorbent material, instead of cellulose fiber, could for example be polyester, polypropylene or other synthetic fibers or mixtures of natural fibers such as cotton or wool with synthetic fibers.

In short, the materials of the back sheet 3, the absorbent bodies 4 and the cover sheet 7 can all be conventional; it is their arrangement and relationship to each other, as well as the method and apparatus for their assembly, that patentably characterize the present invention.

The pad 1 can also be provided with one or more pockets forming a margin 11, again filled with absorbent material. Outwardly of margin 11 is a border 13 in which, as in channels 9, cover sheet 7 is directly secured to back sheet 3.

The resulting pad 1, if an incontinence pad, can be of conventional size and shape for such purpose, having a length and width, for example, of about 75 cm and 60 cm, respectively.

In use, the pad 1, if an incontinence pad, is placed beneath the incontinent person, whose weight is borne by the filled pockets 5, leaving open the channels 9 between them. Liquid from the person's body readily penetrates the liquid-pervious cover sheet 7 and is absorbed by the immediately subjacent bodies 4 of absorbent material. When these are full, then the excess liquid passes along the channels 9 to the nearest dry pockets 5, where the liquid is absorbed from the channels 9 through the side walls of those pockets that form the sloping walls of the channels 9 and into the dry absorbent material in those next pockets 5. This can proceed until substantially all the pad is saturated. Only thereafter will there be danger of liquid leakage or spillage. In the meantime, however, maximum utilization of the ability of the pad to absorbent liquid, has been achieved.

Figure 4:
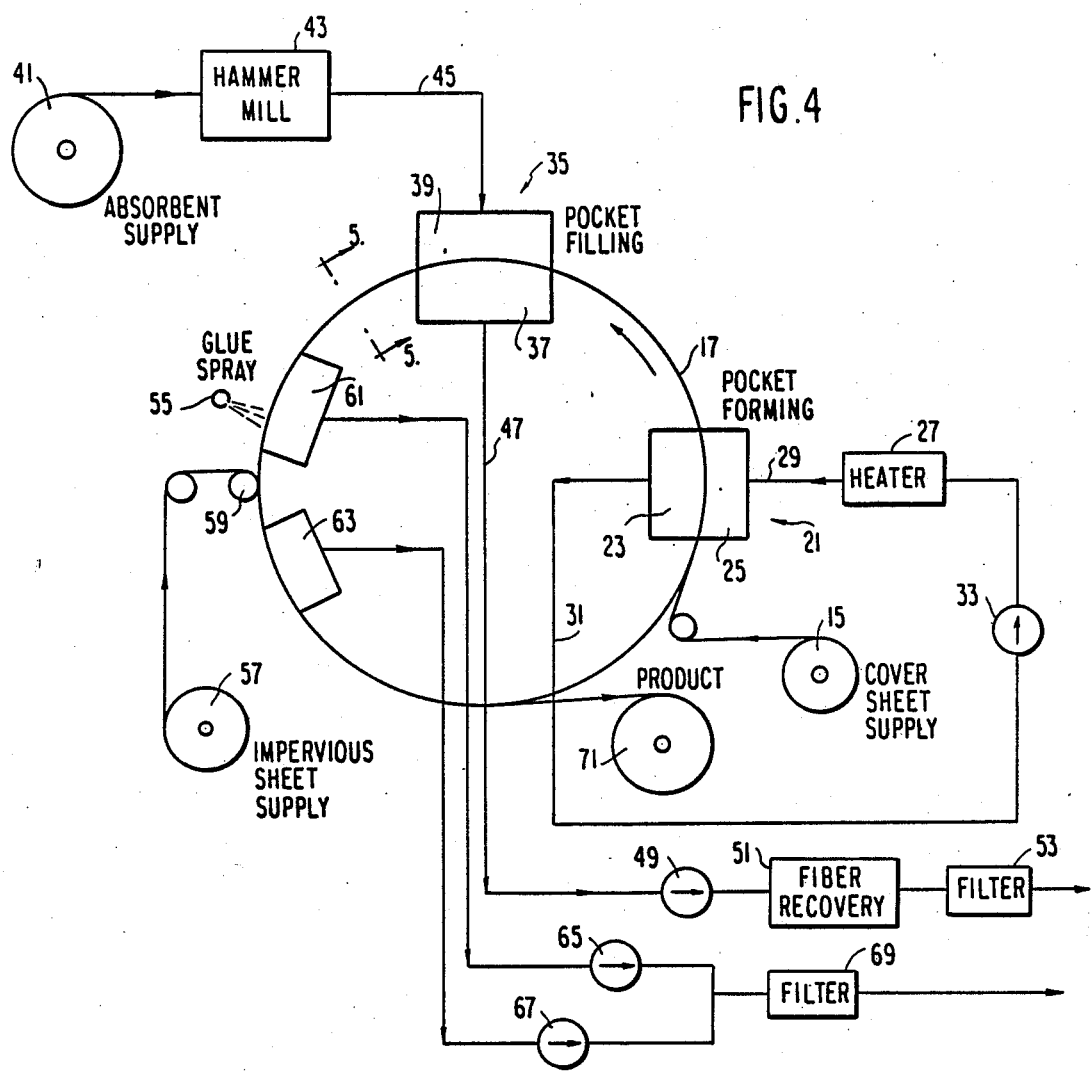
FIG. 4 is a diagrammatic view of apparatus for practicing the method and producing the product of the present invention.
Figure 5:
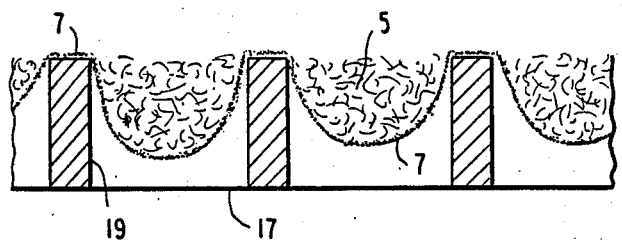
FIG. 5 is an enlarged fragmentary cross sectional view on the line 5—5 of FIG. 4.

Referring now to FIGS. 4 and 5, there is illustrated a method and apparatus for producing pads according to the present invention.

As can be seen from FIG. 4, a supply 15 comprising a roll of cover sheet material feeds an air-pervious and liquid-impervious cover sheet material as described above in an indeterminate length to the periphery of a rotating multi-perforate drum 17 that turns counterclockwise as seen in FIG. 4. The periphery of drum 17 is penetrated by a plurality of holes 19 of the same size and shape and arrangement as the pockets 5 it is desired to form. The thickness of drum 17 in a radial direction is at least as great as the maximum depth of the pockets 5 it is desired to form, so that the pockets 5 do not protrude radially inwardly beyond the radially inner surface of the drum. It is not necessary that drum 17 have end walls.

Means (not shown) are provided for driving drum 17 in rotation at the desired velocity of rotation, which is the same peripheral speed as the speed of linear feed of the material for cover sheet 7. Therefore, there is substantially no movement of the cover sheet material on and relative to the drum between the time the cover sheet material first contacts the drum and the time the final product leaves the drum.

The cover sheet material on the periphery of the drum then moves with the drum into a pocket-forming station 21 in which the cover sheet is given its final shape in the course of producing empty pockets. How those pockets are formed may depend on the material of the cover sheet. The cover sheet material can be, as previously indicated, a thermoplastic synthetic resin, e.g. polypropylene fibers. In this case, the pockets can be formed by drawing a vacuum in a radially inward direction against the underside of the cover sheet material, so as to draw heated air through the cover sheet material. This heated air will be at a temperature a little above the softening temperature of the thermoplastic material and will soften the thermoplastic material, so that the resistance offered by the softened cover sheet material to the passage of air will cause the thermoplastic material to deform into a radially outwardly concave pocket within each hole 19 through drum 17.

In the case of polypropylene, whose softening temperature is about 120° C., the heated air will preferably have a temperature of about 120° C. to 300° C., e.g. 175° C.

For this purpose, there is provided, immediately downstream of the point at which the cover sheet material first contacts drum 17, a vacuum chamber 23 on the radially inner side of drum 17 and a heated air supply chamber 25 in registry therewith on the outer side of drum 17. Air heated in an air heater 27 passes by conduit 29 into supply chamber 25 and thence passes through the porous cover sheet material, heating and deforming the same as explained above, under the influence of a vacuum in vacuum chamber 23. This heated air then passes via conduit 31 to a fan 33 which recycles the air through heater 27, etc. Fan 33 draws a vacuum in chamber 23 of 50 to 900 mm of water, preferably 400-600 mm. Heater 27 is regulated by a conventional thermostat (not shown) thereby to maintain the desired air temperature. Fan 33 is adjustable as to its throughput, thereby to control the depth of the pockets formed.

Upon further rotation of the drum 17, the cover sheet with pre-formed pockets enters a pocket-filling station 35 comprised as before by a vacuum chamber 37 on the radially inner side of the drum 17, but now with a feed chamber 39 not for heated air but for absorbent material. If the absorbent material is, as in the preferred embodiment, a cellulose fiber fluff, then the same can be fed from a supply 41 thereof in which it is rolled up as a batt and fed to a hammer mill 43 in which numerous small rotating hammers break the feed apart to form a fluff which then proceeds via conduit 45 to chamber 39. This method of absorbent fluff supply is entirely conventional and as such forms no part of the present invention.

But this fluff in chamber 39 is drawn down into the pockets by the vacuum in chamber 37, which can have the same values as for chamber 23. The operation in pocket filling station 35 differs markedly from that in pocket forming station 21, in that the pockets are already formed, and in that the formed pockets perform a filter action, letting through the air but retaining the absorbent within the pockets. Commercially available cover sheet materials, particularly non-woven fabrics, are often too fine to allow fibers to pass through. Hence an almost complete separation of fibers from the air that carries them is achieved.

Air is drawn from vacuum chamber 37 via conduit 47 by a fan 49 and fed through a fiber recovery device 51, e.g. a cyclone separator, and thence through a filter 53. The air thus cleaned can be discharged to the atmosphere without creating a health hazard. Fan 49 is adjustable as to its throughput so as to control the amount of absorbent deposited in the pockets.

The supply of absorbent material to chamber 39, and the dwell time of the pockets therein, as well as the setting of fans 49, are such that the pockets are just filled but not overfilled with absorbent material. The absorbent material is strongly drawn into the pockets and held there by the air flow induced by the vacuum in chamber 37, with the result that substantially no absorbent material is left on that portion of the cover sheet that overlies the bridges between the holes 19 of the drum 17. The result is that the drum 17 leaving pocket-filling station 35 has a cross-sectional appearance much as in FIG. 5. As will be seen from that figure, the radially outwardly open pockets 5 are filled but not overfilled with absorbent material, and substantially no absorbent material overlies those portions of the cover sheet 7 that overlie the bridges between holes 19 of drum 17.

Of course, it is also possible to provide a brush or other screed (not shown) to sweep free from any possible absorbent material, the exposed portions of the cover sheet between the pockets.

Turning further, the drum 17 brings the filled pockets to a glue spray 55 for securing the liquid-impervious back sheet 3. The glue for this purpose is preferably a hot melt glue of conventional type for use in disposable diapers and the like. It is applied at a temperature which is for example 110°-250° C. A typical such glue is Hernimelt 8600, from Hernia of Sweden.

The liquid-impervious back sheet 3 is fed from a supply 57 thereof about rollers of which a roller 59 presses the back sheet against those exposed portions of the cover sheet 7 that are backed by the bridges between the holes 19 of the drum 17. In the illustrated embodiment, the glue is sprayed against those bridge backed exposed portions of the cover sheet (as well as against the exposed surface of the absorbent in the pockets 5). Alternatively, of course, the glue spray 55 can be directed against the impervious sheet 3 itself, for example as it passes about the roller 59.

In any event, the rate of spray application of the melt adhesive is 1-20 g/m$^2$, preferably 3-5 g/m$^2$.

Still another alternative is to dispense with the glue spray altogether and to bond the sheets 3 and 7 together along the locations of the channels 9, by heat welding. In this case, the roll 59 will be heated to perform a conventional heat sealing operation. To facilitate this operation, a coextruded film can be used for the base sheet 3, having a thin layer of easily heat-sealable material on the side thereof that will contact the cover sheet. For example, a base sheet of Neste polyethylene DFDS 0601 of a thickness 0.010-0.025 mm could be used, faced with a thinner layer of Surlyn 1652 from Dupont of a thickness of 0.003-0.010 mm.

A further vacuum chamber 61 is provided on the radially inner side of drum 17 opposite glue spray 55, to reduce fumes and blow back from the glue spray. Another vacuum chamber 63 is provided on the radially inner side of drum 17 immediately downstream of roller 59. Because the impervious sheet 3 is now in place, this last vacuum chamber tends to draw the impervious sheet 3 tightly against the drum, thereby to hold the cover sheet and back sheet firmly together until they have cooled to the point that the adhesive is hardened.

Fans 65 and 67 provide the necessary suction in chambers 61 and 63, respectively, and feed to a filter 69 for the removal of particles from the airstream, after which the cleansed airstream can be discharged to the atmosphere without danger to the environment.

The finished product finally leaves the periphery of drum 17 and can be gathered on a roll 71, eventually to be cut to the desired size of pads by conventional cutting means (not shown), or can be directly cut to size without rolling.

Whether the material of the cover sheet is or is not thermoplastic, it can be mechanically preformed to the shape of the required pockets by passing it between embossing rolls or belts or the like, it being possible to use the drum 17 itself as one of the embossing rolls.

FIGS. 6 and 7 show another embodiment of the present invention, in which the pockets are mechanically formed. Such mechanical formation can of course be conducted even with a thermoplastic cover sheet material, but is particularly useful when the material is non-thermoplastic, for example cellulose linen, cotton, etc.

In order to form pockets mechanically, it is necessary to provide an excess of material both transversely and longitudinally of the cover sheet material; and the pockets will be formed from this excess. Thus, although the technique for forming pockets mechanically can result in a certain lateral displacement of the woven or nonwoven fibers of a fibrous cover sheet material, nevertheless, it is contemplated that there will be no substantial deformation of the cover sheet material during pocket formation other than by flexing the same.

It is preferred to provide this excess material in two stages, one of which provides the excess laterally and the other of which provides the excess longitudinally of the cover sheet material. To this end, the cover sheet material leaving the supply thereof passes about a roller 73 which has in its outer periphery a plurality of parallel equally-spaced annular grooves of semi-circular cross sectional configuration. A series of rods 75-85 are disposed one in each of those grooves. The cover sheet material passes between those rods and the side walls of the grooves, thereby to crease the cover sheet material in a longitudinal direction. Means (not shown) are provided for adjustably mounting the rods relative to the roller 73, thereby to vary the depth to which the rods penetrate the grooves and hence the amount of lateral excess to be drawn into the cover sheet material.

So that the rods 75-85 will not compete with each other for material, it is provided that they contact the material sequentially rather than simultaneously. To this end, the material is first contacted by a single central rod 75 which is equidistant from both ends of roller 73, subsequently by a pair of rods 77 disposed one on each side of rod 75, next by a pair of rods 79 disposed on opposite sides of the rods 77, and so on until the material finally contacts the rods 85 that are disposed adjacent the edges of the material, in the two grooves that are the endmost grooves on roller 73.

The material leaving roller 73 will therefore have a somewhat undulate form in a transverse direction and will of course be substantially narrower than the flat sheet material which approached roller 73. This undulate form need not be preserved as such: in passing over subsequent rolls, the material can be flattened whereby it will be creased or folded. It suffices only to provide a well-distributed excess of material, it not being necessary to try to preserve any particular pocket configuration prior to arrival of the material on the drum 17.

From the roller 73, the material next passes between a pair of coacting belts 87, 89 which have on their opposed surfaces mating ribs as seen in FIG. 7. These mating ribs impart to the material a corrugation in the direction opposite that of the rollers 73 and rods 75-78, transversely of the length of the material, thereby providing a longitudinal excess of the material. Belt 87 is traversed by holes 91 and belt 89 by holes 93 to provide free flow of air through the belts and the cover sheet material as they pass about a vacuum chamber 95 evacuated through a suction conduit 97. Holes 91 obviously enable the vacuum chamber to hold the cover sheet material against belt 87 until the material reaches drum 17; and holes 93 prevent belt 89 from being sucked against belt 87 during the time the two belts are in contact with each other and overlie vacuum chamber 95.

The cover sheet material, with excess both laterally and longitudinally, next is transferred from belt 87 to drum 17. A vacuum chamber 99, disposed on the side of drum 17 opposite the cover sheet material and evacuated through a suction conduit 101, then draws the cover sheet material down into the holes 19 through drum 17, whereby the pockets 5 are mechanically formed. These pockets are then mechanically held by suction in their formed condition as the drum 17 turns counterclockwise as seen in FIG. 6 until the formed pockets reach the adjacent edge of vacuum chamber 37 whereupon the pockets begin to be filled as previously described.

Both in vacuum chamber 95 and vacuum chamber 99, the vacuum to be drawn can be, for example, 500–1500 mm of water, most preferably about 1000 mm of water. Of course, as this vacuum performs a purely mechanical function, these values are illustrative only and are subject to substantial variation.

From a consideration of the foregoing disclosure, therefore, it will be evident that all of the initially recited objects of the present invention have been achieved.

Although the present invention has been described and illustrated in connection with preferred embodiments, it is to be understood that modifications and variations may be resorted to without departing from the spirit of the invention, as those skilled in this art will readily understand. Such modifications and variations are considered to be within the purview and scope of the present invention as defined by the appended claims.

What is claimed is:

1. An absorbent pad comprising a liquid-impervious back sheet, a plurality of bodies of liquid-absorbent material disposed on one surface of the back sheet, and a liquid-pervious cover sheet covering said bodies of absorbent material and directly secured to the back sheet along lines which separate said bodies of absorbent material, these lines being substantially free from said absorbent material.

2. A pad as claimed in claim 1, in which at least most of said bodies are islands surrounded on all sides by said lines.

3. A pad as claimed in claim 1, in which said cover sheet is adhesively bonded to said back sheet along said lines.

4. A pad as claimed in claim 1, in which said cover sheet is cohesively secured to said back sheet along said lines.

5. A pad as claimed in claim 1, in which said back sheet is substantially flat and said cover sheet has pockets therein in the shape of and containing said bodies.

* * * * *